(12) United States Patent
Lali et al.

(10) Patent No.: US 8,338,139 B2
(45) Date of Patent: Dec. 25, 2012

(54) METHOD FOR PRODUCTION OF FERMENTABLE SUGARS FROM BIOMASS

(75) Inventors: Arvind Mallinath Lali, Mumbai (IN); Pooja Devidas Nagwekar, Mumbai (IN); Jayesh Suman Varavadekar, Mumbai (IN); Prathamesh Chandrashekhar Wadekar, Mumbai (IN); Swapnali Subhash Gujarathi, Mumbai (IN); Rajeshwar Dattatray Valte, Mumbai (IN); Sachinkumar Hiraman Birhade, Mumbai (IN); Annamma Anil Odaneth, Mumbai (IN)

(73) Assignee: Chemical Engineering Department, Institute of Chemical Technology (Deemed University), Mumbai (IN)

( * ) Notice: Subject to any disclaimer, the term of this patent is extended or adjusted under 35 U.S.C. 154(b) by 0 days.

(21) Appl. No.: 13/305,063

(22) Filed: Nov. 28, 2011

(65) Prior Publication Data

US 2012/0115192 A1 May 10, 2012

Related U.S. Application Data

(63) Continuation of application No. PCT/IN2010/000355, filed on May 26, 2010.

(51) Int. Cl.
  *C12P 19/20* (2006.01)
  *C12P 19/14* (2006.01)
  *C12P 19/02* (2006.01)
(52) U.S. Cl. .............................. 435/96; 435/99; 435/105
(58) Field of Classification Search .................. None
  See application file for complete search history.

(56) References Cited

U.S. PATENT DOCUMENTS

| 4,200,692 | A | 4/1980 | Puls et al. |
| 227,162 | A | 7/1993 | Ferrari et al. |
| 5,348,871 | A | 9/1994 | Scott et al. |
| 5,637,502 | A | 6/1997 | Scott et al. |
| 5,932,452 | A | 8/1999 | Mustranta et al. |
| 6,423,145 | B1 | 7/2002 | Nguyen et al. |

FOREIGN PATENT DOCUMENTS

| EP | 2 017 349 | 1/2009 |
| WO | WO 2006/063467 | 6/2006 |
| WO | WO 2006/110901 | 10/2006 |
| WO | WO 2008/065433 | 6/2008 |
| WO | WO 2008/076159 | 6/2008 |
| WO | WO 2008/113585 | 9/2008 |
| WO | WO 2008/155639 | 12/2008 |
| WO | WO 2009/004950 | 1/2009 |
| WO | WO 2009/046524 | 4/2009 |
| WO | WO 2009/098618 | 8/2009 |

OTHER PUBLICATIONS

International Search Report in PCT Application No. PCT/IN 2010/000355, (Sep. 5, 2011).
Carvalheiro, F., et al., "Hemicellulose biorefineries: a review on biomass pretreatments," *Journal of Scientific and Industrial Research*, 67(11):849-864 (Nov. 1, 2008).
Reese, E.T., et al., "Producton of β-D-xylopyranosidases by fungi," *Can J. Microbiol.*, 19:1065-1074 (1973).
Himmel, M.E., et al., "Biomass Recalcitrance: Engineering plants and enzymes for biofuels production," *Science*, 315: 804-807 (2007).
Bothast and Saha, "Ethanol Production from Agricultural Biomass Substrates," *Advances in Applied Microbiology*, 44:261-286 (1997).
Beguin, P. et.al., "The biological degradation of cellulose," *FEMS Microbiological Review*, 13:25-58 (1994).
Tilbeurgh Ven H., et al., "Studies of the cellulytic system of *Trichoderma reesei* QM 94014," *European Journal of Biochemistry*, 189:553-559 (1989).
Dourado F., et al, "Studies on the properties of Celluclast/Eudragit L-100 conjugate," *Journal of Biotechnology*, 99:121-131 (2002).
Busto MD et al., "Stabilisation of cellulases by cross-linking with glutaraldehyde and soil humates," *Bioresource Technology*, 60:27-33 (1997).
Woodward J., "Immobilized cellulases for cellulose utilization," *Journal of Biiotechnology*, 11:299-312 (1989).
Khare and Gupta, "A Crosslinked Preparation of *E. coli* β-D-Galactosidase," *Applied Biochemistry and Biotechnology*, 16:1-13 (1987).

*Primary Examiner* — Nashaat Nashed
(74) *Attorney, Agent, or Firm* — Brinks Hofer Gilson & Lione

(57) ABSTRACT

A process for production of fermentable sugars from biomass using multi-enzyme multi-step system is provided herein. The process disclosed in the present invention provides high yielded sugars in less time period. The multi-enzyme system disclosed in the present invention converts celluloses, hemicelluloses and/or mixture thereof to fermentable sugar with higher efficiency and better economics than the process known in the prior art. Cellulose and hemicelluloses fractions derived from natural sources such as any lignocellulosic biomass are saccharified in a shortened time with higher conversion rates of intermediates with modified enzymatic compositions/groups of the Multi-enzyme system to enhance the rate thus providing an economical cellulose and hemicellulose saccharification process.

15 Claims, No Drawings

METHOD FOR PRODUCTION OF FERMENTABLE SUGARS FROM BIOMASS

RELATED APPLICATIONS

The present patent document is a continuation application of PCT Application Serial No. PCT/IN2010/000355, filed May 26, 2010, designating the United States and published in English, which claims priority from provisional applications numbers 1299/MUM/2009 filed on May 26, 2009 and 1314/MUM/2009 filed on May 29, 2009. All of the foregoing applications are hereby incorporated by reference.

FIELD OF INVENTION

The present invention relates to the field of production of fermentable sugars from biomass for production of biofuel and other by-products.

BACKGROUND OF INVENTION

Lignin and two polysaccharides hemicellulose and cellulose form the three major components of plants physiology and are collectively called as lignocellulose. Of these three, cellulose and hemicellulose are basically polymers of sugar monomers like glucose, xylose, galactose, arabinose etc. Therefore, cellulose and hemicellulose derived from plant residues, if hydrolyzed to monomeric sugars, can form a useful and abundant renewable source of raw material for a variety of useful chemicals and biochemicals. Conversion of this generally tightly compacted composite lignocellulosic material to sugar is accomplished by a composite process known as hydrolysis and saccharification. Worldwide research on saccharification processes for the conversion of lignocelluloses to sugars has followed three major approaches. First is chemical hydrolysis, the second is thermal hydrolysis and the third is enzymatic hydrolysis.

In a general chemical hydrolysis process, hemicellulose is separated in the first step from the lignocellulose composite material by the action of an acid or alkali. The plant material/mass is mixed with a dilute solution of an acid or alkali and then heated. This process releases and "hydrolyzes" the hemicellulose. Hydrolysis of hemicellulose produces pentose sugars (C5 sugars) as well as some hexose sugars (C6 sugars). The second step is a higher temperature acid hydrolysis process that hydrolyzes the plant material cellulose, producing almost solely C6 (hexose) sugars, and lignin. The C6 sugars, when separated substantially from lignin, are readily fermentable, and the recovered lignin can be used for process heat or making other products.

Two stage acid hydrolysis processes have been used for many years. However, it is now known that the acid processes also produce chemicals other than sugars that not only represent a process loss but also lead to problems later in the use of the sugars in downstream processes like fermentation to useful products like lactic acid, alcohols, organic acids etc. Another major problem with these systems has been that the acid must either be recovered for re-use or it must be neutralized through the use of lime in order to mitigate effluent and pollution problems.

Autothermal processes on the other hand do not make use of any chemicals and thus are cleaner processes. High temperatures and short exposures like used in Steam Explosion processes, results in breakdown of the lignocellulosic biomass into monosugars and hydrolyzed lignin. However, such processes suffer from the drawbacks of lower sugar yields, formation of unwanted side-products that are inhibitory to downstream processes, and are energy intensive.

Use of enzymes, generally preceded by some or the other mild pretreatment steps, provides much cleaner and low energy process for cellulose and hemicellulose hydrolysis and saccharification and finally provides better quality end products i.e. sugars in higher yields.

Several enzymes are known to specifically, or non-specifically, hydrolyze plant cell wall polysaccharides. Such enzymes derived from culture filtrates of microorganisms have found large scale applications for hydrolysis of cell wall components (Reese, E. T. et al, Can. J. Microbiol. 19, 1973, 1065-1074). Microorganisms produce numerous proteins, and some also produce cellulose and/or hemicellulose splitting enzymes. Most reports and technologies make use of these catalytic enzymes in free soluble form that cannot be recovered for reuse. Further, often the substrates namely cellulosic and/or hemicellulosic polymers and products of hydrolysis thereof, have tendencies to 'inhibit, the enzymes' actions. Such a use of these enzymes makes them less attractive for use on a commercial scale or makes the use of the enzymes more expensive than often desired. Therefore, for reasons of cost, the amount of enzymes used per unit weight of cellulose and/or hemicellulose hydrolyzed is often kept to a minimum, which in turn reduces the rate of hydrolysis reactions and increases the reaction times.

For the reasons stated above, and for other reasons stated below which will become apparent to those skilled in the art upon reading and understanding the present specification, there is a significant need in the art for systems and methods that provide for improved biomass conversion to sugars in a cost-effective manner. Shortcomings of the enzyme process can be alleviated making it the obvious choice for new process development.

Cellulose and hemicellulose are the first and second most abundant polysaccharides in nature. Cellulose represents anywhere from 30 to 60% while hemicelluloses represent about 20-35% of lignocellulosic biomass (LBM) such as corn fiber, corn stover, wheat straw, rice straw, and sugarcane bagasse. While cellulose is an almost homogeneous polymer comprised of several hundreds to thousands D-glucose units linked through 1,4 β-glycosidic linkages, hemicelluloses are heterogeneous polymers of pentoses (xylose, arabinose), hexoses (mannose, glucose, galactose), and sugar acids. Hardwood hemicelluloses contain mostly xylans, whereas softwood hemicelluloses contain mostly glucomannans. Xylans of most plant materials are thus heteropolysaccharides with homopolymeric backbone chains of 1,4-linked β-D-xylopyranose units. Besides xylose, xylans may also contain arabinose; glucuronic acid or its 4-O-methyl ether; and acetic, ferulic, and p-coumaric acids. The frequency and composition of branches are dependent on the source of xylan while the backbone consists of O-acetyl, α-arabinofuranosyl, α-1,2-linked glucuronic or 4-O-methylglucuronic acid substituents.

For both cellulose and hemicellulose components to be efficiently converted to their monosugar components these must first be extracted from the lignocellulosic complex. Enzymatic saccharification of these two components using cellulases and hemicellulases is the preferred method due to rapid action of the enzyme, and negligible substrate loss and side product generation. Both cellulose and hemicellulose in intact LBM however, are not accessible to enzymatic hydrolysis. And therefore pretreatment of the LBM to render these amenable to enzyme action is mandatory (Himmel, M. E. et al, 2007; Bothast and Saha, 1997). While cellulose, though a homopolymer, is a far more bulkier, crystalline and compact molecule, the structure of hemicellulose is more complex as it comprises of pentoses, some hexoses and side chain groups such as acetyl and uronic acids. Thus, enzymatic hydrolytic action for both cellulose and hemicellulose requires combined action of more than one enzyme. For cellulose hydrolysis the crystal structure of cellulose needs to be partially or wholly rendered amorphous after which a mixture of exo and endo cellulases is required for conversion of the polymeric cellulose to much smaller oligomeric molecules. On the other hand, in case of hemicellulose, the presence of side chain groups hampers the action of major backbone depolymerizing enzymes i.e. exo and endo xylanases, and mannanases. To address this problem accessory enzymes such as α-L-arabinofuranosidase, α-glucuronidase, acetylxylan esterase, ferulic acid esterase, and p-coumaric acid esterase which have the ability to hydrolyze the side chains have to be present with the major hemicellulases to achieve complete degradation of hemicellulose to obtain high yields of monosaccharide sugars (Biely and Tenkanen, 1998).

As a result of such scenario, cellulase and hemicellulase preparations used for depolymerizing or hydrolyzing cellulose and hemicellulose, respectively, contain a myriad of major and minor enzymes that all act together.

However, on the other hand, it is now well recognized that, the starting and intermediate substrates occurring during the sequential but complicated process of polymer hydrolysis, tend to act as partial or complete inhibitors of the enzymes present in the mixture preparations used (Beguin P et. al, (1994), FEMS Microbiological Review, 13, 25-58 and Ven H Tilbeurgh et al, Studies of the cellulytic system of *Trichoderma reesei* QM 94014 (1989), European journal of Biochemistry, 189, 553-559). As a result of this fact, and the fact that one may not want to use excessive quantities of enzymes for cost reasons, the enzymatic saccharification processes for both cellulose and hemicellulose are long duration reactions requiring 24 to 48, and often more, hours for completion. It has long been accepted that enzymes are truly efficient catalysts. However, since derived from biological sources and purified, at least partially, and on account of their inherently complex, fragile and sensitive nature, enzymes are expensive and unstable. This has put severe limitations on the spectrum and scale of applications of enzymes in industry (F. Dourado et al, 2002, Journal of Biotechnology, 99, 121-131). Several methods have been devised to render the enzymes stable and less expensive for use for production scale applications. Thus, new enzymes, including cellulases and hemicellulases, have been developed and manufactured such that they are stable to wide temperature, pH and other harsh conditions like presence of inhibitors (Khare and Gupta, 1988, Applied Biochemistry and Biotechnology, 16, 1-15, Busto et al, Bioresource Technology, 1997, 60, 27-33). However, despite these efforts, these enzymes today contribute significantly to the cost of conversion of cellulose and hemicellulose to simple sugars.

One way of reducing enzyme cost is to use the enzymes in immobilized form, or in a form, or way, that permits reuse of enzymes over many cycles, or over extended periods of time. Thus, in a reusable form or way, the enzymes are retained in the reactor, while the substrate/s and product/s flow in and out, in batch or continuous fashion. However, use of an enzyme in immobilized form on a solid support, requires that reactants (or substrates) and products are in soluble form to facilitate the reaction. Further, when using enzymes for reactions involving polymeric reactants and products (like cellulose and hemicellulose), the accessibility of the enzymes in the pores of the immobilization support becomes rate limiting and the reactions become too slow to be of practical use (Woodward J. 1989, Journal of biotechnology, 11, 299-311).

This, and the fact that cellulose is an insoluble solid and hemicelluloses are polymeric with low solubility in water as well, has prevented use of cellulases and hemicellulases in recyclable and/or immobilized forms.

U.S. Pat. No. 4,200,692 discloses a process for the production of xylose by enzymatic hydrolysis of xylan wherein the enzymes are immobilised separately but incubated together and, the xylan solution is broken to xylobiose and xylose and acid sugars. After 4 hours total hydrolysis to xylose and 4-O-methylglucuronic acid is claimed. US2008/065433 discloses a process for obtaining fuel ethanol by using agricultural and agroindustrial waste materials composed of lignocellulose, and especially sugar cane bagasse. The hemicellulose fraction is submitted to mild hydrolysis with sulphuric acid, and the solid material from this hydrolysis is submitted to a process of saccharification (enzymatic hydrolysis) with simultaneous rapid alcoholic fermentation under conditions which allow a significant increase in conversion to alcohol in a greatly shortened time, approximately 8-32 hrs.

U.S. Pat. No. 6,423,145 discloses a modified dilute acid method of hydrolyzing the cellulose and hemicellulose in lignocellulosic material under conditions to obtain higher overall fermentable sugar yields, comprising: impregnating a lignocellulosic feedstock with a mixture of an amount of aqueous solution of a dilute acid catalyst and a metal salt catalyst, loading the impregnated lignocellulosic feedstock into a reactor and heating for a sufficient period of time to hydrolyze substantially all of the hemicellulose and greater than 45% of the cellulose to water soluble sugars; and recovering the water soluble sugars.

US2009/098618 discloses a method for treating plant materials to release fermentable sugars. Lignocellulosic materials are subjected to disc refining together with enzymatic hydrolysis to produce sugar rich process stream that may subsequently be subjected to fermentation to produce biofuels and chemicals.

U.S. Pat. No. 5,348,871 discloses a process for converting cellulosic materials, such as waste paper, into fuels and chemicals utilizing enzymatic hydrolysis of the major constituent of paper, cellulose. Waste paper slurry is contacted by cellulase in an agitated hydrolyzer. The glucose produced from hydrolyzer is fermented to ethanol in a continuous, columnar, fluidized-bed bioreactor utilizing immobilized microorganisms. The process disclosed in the patent requires 'many hours to days for acceptable yields'.

U.S. Pat. No. 5,637,502 discloses a batch process for converting cellulosic materials into fuels and chemicals, such as sugars and ethanol, utilizing enzymatic hydrolysis of cellulose. Waste paper slurry is contacted by cellulase in an agitated hydrolyzer. An attritor and a cellobiase reactor are coupled to the agitated hydrolyzer to improve reaction efficiency. Additionally, microfiltration, ultrafiltration and reverse osmosis steps are included to further increase reaction efficiency and recycling of the enzymes. The resulting sugars are converted to a dilute ethanol product in a fluidized-bed bioreactor utilizing a biocatalyst, such as microorganisms. The time of hydrolysis of paper cellulose is about 24 hours.

US227162 discloses a method for lignocellulose conversion to sugar with improvements in yield and rate of sugar production by using ionic liquid pretreatment. However, the time required for complete batch enzymatic hydrolysis is within 16 to 36 hours for two of the representative biomass samples—corn stover, poplar which is a substantially longer period.

U.S. Pat. No. 5,932,452 discloses a process for the hydrolysis of a hemicellulose substrate containing xylo-oligomers, obtained from steam exploded plant biomass or enzymatically partially pre-hydrolyzed xylan, with an immobilized enzyme. This process however, has the pre-requisite of producing partially hydrolyzed hemicellulose which in turn needs to be obtained from plant biomass through suitable process such as steam explosion. Steam explosion is a hydrothermal process and is known to produce furfural derivatives that are known to affect both enzymatic conversion, and later fermentation efficiencies.

US2008/076159 discloses methods to produce enzymes or novel combinations of enzymes, which provide a synergistic release of sugars from pre-treated plant biomass. However, the disclosed process does not reduce the saccharification period which is in the range of 24-72 hours.

EP2017349 discloses a method for the direct enzymatic treatment of raw polymeric feedstock and separation of the resulting soluble components. However, there is no mention of recovery and reuse of the enzymes, and the hydrolysis duration is also a prolonged one.

WO/2006/063467 discloses a continuous process system for enzymatic hydrolysis of pre-treated cellulose which comprises introducing aqueous slurry of the pre-treated cellulosic feedstock at the bottom of a vertical column hydrolysis reactor. Axial dispersion in the reactor is limited by avoiding mixing and maintaining an average slurry flow velocity of about 0.1 to about 20 feet per hour, such that the undissolved solids flow upward at a rate slower than that of the liquid. Cellulase enzymes are added to the aqueous slurry before or during the step of introducing. An aqueous stream comprising hydrolysis products and unhydrolyzed solids is removed from the hydrolysis reactor and after solid separation the unhydrolyzed cellulose is recycled. Also provided are enzyme compositions which comprise cellulase enzymes and flocculents for use in the process. In addition, a kit comprising cellulase enzymes and flocculent is described that is said to provide exposure of the enzyme to the substrate. Although the cellulose conversion is better in this case than batch reactor, the time required is 48 hours to 200 at respective enzyme loading of 32 units/g cellulose to 5 units/g cellulose.

WO/2009/004950 discloses that monosaccharide and/or a water-soluble polysaccharide can be produced with a high degree of efficiency by hydrolyzing a cellulose-containing material with a sulfonate-containing carbonaceous material. The used sulfonate-containing carbonaceous material can be reactivated and reused by carbonization and sulfonation, without the need of separating the sulfonate-containing carbonaceous material from the unreacted portion of the cellulose-containing material. This method, which does not use any enzymes, enables to reduce the cost for hydrolysis, can reduce the amount of waste materials, and therefore can contribute to the global environmental conservation.

The concept of enzymatic hydrolysis of cellulose and hemicelluloses is known since long. As described above, most enzymatic hydrolysis processes in use, or reported are batch processes and take 12-48 hrs for complete saccharification. More often, the enzymatic processes remain incomplete resulting in high enzyme cost and slow reactions leading to low throughputs and hence high capital investment in large reactors. While use of higher dosage of enzymes can increase the hydrolysis rate, the cost considerations limit the dosages. Further, dosages of enzymes in typical batch processes are higher than desired on account of inhibitory effects of reaction substrates and products on the enzymes. For this reason, new efficient methods are needed for cellulose and hemicellulose saccharification which will require lower enzyme dosages per kilo of cellulose and hemicellulose, not require high temperatures and pressures, will not generate hazardous byproducts, will be less time consuming, and require less energy, thus making the process more economically viable.

At the scale at which a biomass to sugars plant is expected to operate (typically 100 to 1000 tons biomass/day) large reaction times imply humongous sized enzyme reactors exceeding several 100 KL capacities. It is therefore necessary to speed up the reaction rates thereby increasing volumetric throughputs.

OBJECTS OF THE INVENTION

One object of the present invention is to provide a multi-enzyme multi-step system for complete conversion of hemicellulose, cellulose, and/or a mixture thereof, obtained from any lignocellulosic material including but not limited to agricultural residue, herbaceous material, forestry residue, municipal solid waste, pulp and paper mill residue, paper waste or any other source.

Another object of the invention is to develop an efficient process, in terms of rate of the process and the amount of enzyme used per unit amount of sugars produced, for the enzyme catalyzed hydrolysis of hemicellulose and cellulose, and or any mixture thereof to fermentable sugars, wherein the process is efficient in terms of enzyme cost as well as be time efficient, and adaptable on industrial scale.

It is still further object of the present invention to provide the multi-enzyme system in two, or more, steps for effective saccharification or depolymerization of cellulose and hemicellulose to fermentable sugars.

Yet another objective of the invention is to provide a multi-enzyme system that comprises at least two groups of enzymes, with selection of specific enzymes from specific groups, for two or more step saccharification, the groups being decided by the nature of the enzymes and as described later below.

Another objective of the invention is to provide further the group/s of enzymes to act as accessory enzymes as well as auxiliary enzymes, and which can be added during the process, or along with the first group of enzymes, or second group of enzymes, and or in both the groups of the multi-step process using multi-enzyme system.

It is still further object of the present invention to optimize each of the steps of cellulose and/or hemicellulose saccharification process, with respect to temperature, pressure, pH, solvent used, time of contact and other parameters to achieve more than 90%, or 95% or 98% conversion within a few hours

SUMMARY OF THE INVENTION

One of the aspect of the present invention provides a process of production of fermentable sugars from hemicellulose and/or cellulose using multi-step multi-enzyme system, wherein the process comprises treating hemicellulose and/or cellulose with at least one enzyme of first group of enzymes at a temperature ranging from 30° C. to 90° C. to obtain a first hydrolysate, and treating the hydrolysate obtained in step (a) with at least one enzyme from second group of enzymes to obtain the fermentable sugars; wherein the first group and second group of enzymes are capable of hydrolysing the hemicellulose and/or cellulose Another aspect of the present invention provides a process of production of fermentable sugars from biomass using multi-step multi-enzyme system, wherein the process comprises mixing biomass with 5% to 10% w/v alkali having pH in the range of 12-14 at a temperature ranging from 50° C. to 200° C. under 1.0 to 20 bar pressure for 5 minutes to 2 hrs to obtain a biomass slurry; filtering the biomass slurry to obtain filtrate comprising hemicellulose; and residue comprising cellulose; treating the filtrate with alcohol to obtain a precipitate containing hemicelluloses; washing the residue with water to remove residual alkali to obtain cellulose; washing the precipitate to obtain hemicelluloses; treating the hemicellulose and/or the cellulose thus obtained with at least one enzyme of first group of enzymes at a temperature ranging from 30° C. to 90° C. to obtain a first hydrolysate; and treating the hydrolysate obtained with at least one enzyme from second group of enzymes to obtain the fermentable sugars; wherein the first group and second group of enzymes are capable of hydrolysing the hemicellulose and/or cellulose

DETAILED DESCRIPTION OF THE INVENTION

Definitions

The term "fermentable sugars" used herein refers to all those sugars, and their mixtures, that are water soluble and can be used as carbon substrates by microorganisms.

The term "Hydraulic Retention Time" (HRT) used herein refers to the average time the reactants spend in the reactor system and that is available for the reaction which herein is the hydrolysis of hemicellulose and/or cellulose.

The terms "hemicelluloses" and "celluloses" as used herein respectively refer to enzymatcially hydrolysable hemicelluloses and celluloses derived from any lignocellulosic biomass.

The present invention relates to a multi-step method for production of fermentable sugars using a multi-enzyme system with selectively chosen multi-enzymes to convert hemicelluloses and/or celluloses to fermentable sugars with higher efficiency in terms of time and enzyme utilization and hence better economics than known in the art. Cellulose and hemicelluloses derived from natural sources such as any lignocellulosic biomass, are saccharified in a shortened time with higher conversion rates of intermediates with modified enzymatic compositions/groups of the multi-enzyme system to enhance the rate, and hence economics of the cellulose and hemicellulose saccharification process.

In one embodiment of the present invention there is provided hemicelluloses and celluloses which are rich fractions that are derived from any lignocelluloseic biomass, and that are amenable to enzymatic hydrolysis resulting in more than 90% hydrolysis to respective monosugars without any mechanical and/or chemical treatment within and during the enzymatic hydrolysis.

Cellulose and hemicellulose fractions obtained from fractionation and pretreatment of biomass can be used for the process. Pure cellulose and hemicellulose from the similar or other sources can also be used. In the present invention, cellulose and/or hemicellulose are saccharified in much lower time than generally known due to higher conversion or reaction rates per unit volume of the reactor and the overall amount of enzymes used.

The present invention of a multi-step multi-enzyme depolymerization or hydrolysis process system includes separate and sequential use of enzyme combinations that break down hemicelluloses and celluloses to fermentable sugars and oligosaccharides that can be further converted to useful products. In several possible combinations, the multi-step process achieves conversion of complex carbohydrates like cellulose and hemicellulose into fermentable sugars, and which together are referred to herein as "saccharification".

Owing to the complex structure of polymeric hemicelluloses and celluloses, several different types of enzymes are needed for their enzymatic degradation or modification. Enzymes in combinations or mixtures, can degrade the sugar polymers namely cellulose and hemicelluloses to simple or oligomeric sugars. Most available enzymes for such processes are indeed combinations or mixtures of enzymes obtained from microorganisms, plants, or other organisms; and synergistic enzyme mixtures comprising enzymes or multi-enzyme products from different, or same, microorganisms, plants or other organisms or the enzymes and mixtures thereof, and can be prepared indigenously and/or obtained commercially.

One of the embodiments of the invention relates to the enzymes that can be used in the invention that are of microbial origin wherein the microorganisms can be, but not limited to, genetically engineered, or natural. These enzymes are, for the purpose of this disclosure, broadly classified into two groups as follows for the two classes cellulases and hemicellulases.

The First group of enzymes comprises of endo-glucanase, exo-glucanase, endo-xylanase, exo-xylanase, mannanase and galactanase from any known source. These enzymes belong to the exo-acting and endo-acting hydrolytic enzymes family, which is characterized by their ability to break down different polysaccharides to produce short-chain oligosaccharides. These enzymes are produced by fungi, bacteria, yeast, marine algae, protozoans, snails, crustaceans, insect, seeds, etc., but the principal commercial sources are filamentous fungi like *Aspergillus niger, Trichoderma reesei* etc. Xylanases can be isolated from psychrophilic microorganisms. Production of xylanases, β-mannanases, arabinanases, and pectinases can be, for example, done by using the thermophilic fungus *Thermomyces lanuginosus*. The mesophilic fungus *Trichoderma harzianum* strain T4 produces extracellular xylanase and mannanase activities when grown in the presence of oat (Avena sativa)-spelt xylan and wheat bran as the carbon sources respectively. Xylanase and Mannanase can be obtained from *Streptomyces galbus* NR. Sources of cellulases, for example, glucanases include fungi like *Aspergillus niger, Trichoderma reesei, Pharochaete chyrosporium, Fusarium solani, Trichoderma konigii, Sclerotiom rolfsii*, etc.; bacteria like *Sporotrichum pruniosum, Arthrorhizopus* sp., *Clostridium thermocellum, Ruminococcus albus, Streptomyces* spp, etc.

The Second group of enzymes comprises of xylosidase, mannosidase and glucosidase. These enzymes belong to the glycosidase enzyme family, which break down the oligosaccharides that are released by exo-acting and endo-acting hydrolytic enzymes, into monomeric sugars. Xylosidase and/or the enzymes from the same group as well as accessory enzymes are generally produced along with xylanase or the main enzyme. Similarly, glucosidase and/or the enzymes from the same group as well as accessory enzymes are also generally produced along with glucanase/s or the main enzyme. For example *Piptoporus betulinus*, a common wood-rotting fungus, produces endo-1,4-beta-glucanase (EG), endo-1,4-beta-xylanase, endo-1,4-beta-mannanase, 1,4-beta-glucosidase (BG), 1,4-beta-xylosidase, 1,4-beta-mannosidase and cellobiohydrolase activities. The fungus produces mainly beta-glucosidase and beta-mannosidase activity in its fruit bodies, while higher activities of endoglucanase, endoxylanase and beta-xylosidase are found in fungus-colonized wood. β-glucosidases for cellobiose and cellulose oligomers hydrolysis can be obtained from microorganisms like *Piromyces* sp, *Fusarium oxysporium* etc.

However xylosidase and its family enzymes can be generated and further purified from some specific microorganism from crude extracts. For example, β-D-Xylosidase is produced in maximum yield from *Humicola grisea* var. *thermoidea*. β-glucosidase and β-xylosidase can also be produced from a yeast-like *Aureobasidium* sp. Few other examples include bacteria such as *Agrobacterium tumefaciens* C58, *Bacillus halodurans* C-125, *Bacillus subtillis* 168, *bifidobacterium longum* NCC2705, *Caulobacter crescentus* CB15, *Clostridium acetobutylicum* ATCC 824, *Streptomyces coelicolor* A3(2), *Thermotoga maritima, Xanthomonas axonopodis* pv. Citri str. 306, *Xanthomonas campestris* pv. campestris str. ATCC 33913, *Cellulomonas fimi, Cellvibrio japonicas, Geobacillus stearothermophilus* T-6, *Geobacillus stearothermophilus* 21, *Penicillium wortmanni*, and *Bacillus pumilus.*

The available and commercial preparations of both cellulases and hemicellulases from different sources are combinations, in different proportions, of the various enzymes including the enzymes from the two groups described above.

In the present invention, hemicellulose and cellulose, or any mixture thereof is saccharified in two or more steps involving enzymes from the above two groups. The First step uses an enzyme preparation that contains at least one enzyme from first group, and may or may not contain other enzymes from the same and second group. In the Second step, the enzyme preparation used contains at least one enzyme from the second group, and which may or may not contain one or more enzymes from the first group. Auxiliary enzymes such as amylases, proteases, lipases, glucuronidases etc. can be optionally added to both or one of the two steps for enhanced rate of hydrolysis. Auxiliary enzyme(s) or auxiliary enzyme mixture disclosed herein are defined as any enzyme(s) that increase or enhance the rate of saccharification of celluloses or hemicelluloses.

It is obvious that a person skilled in the art can produce enzymes of the two groups from any natural or genetically modified organism such as plant, bacteria, yeast or fungi.

In one of the embodiments of the invention, the enzymes of the two groups are generally components of most enzyme preparations commercially available and obtained as fermentation products but these enzymes can be subjected to separation steps prior to use.

In one embodiment, the hemicellulose and cellulose can be obtained from biomass using one or more techniques such as physical, chemical, or physicochemical processes like, thermal treatment, hydrothermal treatment, organosolv treatment, steam explosion treatment, lime impregnation with steam explosion treatment, hydrogen peroxide treatment, hydrogen peroxide & ozone treatment, acid treatment, dilute acid treatment, alkali treatment, heat treatment, or ammonia fibre explosion treatment.

Biomass includes virgin biomass and/or non-virgin biomass such as agricultural biomass, forest waste, commercial organics, construction and demolition debris, municipal solid waste, waste paper and yard waste. Common forms of biomass include trees, shrubs and grasses, wheat, wheat straw, sugar cane bagasse, corn, corn stover, corn kernel including fiber from kernels, products and by-products from milling of grains such as corn, rye, oat bran, wheat and barley (including wet milling and dry milling) as well as municipal solid waste, waste paper and yard waste. The biomass can also be or include, but is not limited to, herbaceous material, agricultural residues, forestry residues, municipal solid wastes, waste paper, and pulp, and paper mill and oil mill residues.

Surprisingly, in the present invention, it was found that the hydrolysis of hemicelluloses and/or celluloses to the fermentable sugars carried out using a multi-enzyme system in two steps increased the overall rate of reactions and therefore reduced the time of the process to produce the fermentable sugars. In particular, when at least one enzyme from the first group of enzymes, and at least one enzyme from the second group of enzymes are added in stepwise manner then the saccharification time reduces 5 to 8 fold compared to the known processes. Contrary to this it was found that when at least one enzyme from the first group of enzymes (glycanases/xylanases) is added along with at least one enzyme from the second group of enzymes (glucosidases/xylosidases) in the reaction medium in the same single step, the initial rate of reaction is high. However, the reaction becomes slow after some time and the total conversion takes more than 24 hrs at the levels of reported enzyme dosages of about 10 enzyme units/g hemicellulose and/or cellulose. One unit of the enzyme is defined as the amount of enzyme that liberates one micromole equivalent of glucose/minute/mL of reaction volume.

In the multienzyme multi-step reaction disclosed in the present invention, the enzymes utilized may be prepared by the methods well known in the art, or may be obtained commercially.

One of the embodiments of the invention is the first step wherein at least one enzyme is specifically selected from the first group. Thus enzyme preparation used in the first step comprises at least one enzyme derived/selected from group comprising of endo and exo cellulases and/or xylanases, and any mixtures thereof. Similarly, in the second step, at least one enzyme is specifically selected from the second group of enzymes comprising of xylosidase, mannosidase and/or glucosidase, and any mixtures thereof. The reason for such sequential selection of specific enzymes from specific groups, and using such enzymes or group of enzymes, in a step wise manner is that the products of glycanases and xylanases interfere with, or inhibit the action of glucosidases and xylosidases, and such interference reduces the activity of the added enzymes and slows down the overall rate of hydrolysis or depolymerization reaction.

Further embodiment of the invention relates to overcoming of the limitations of the traditional combined use of the first group and the second group enzymes, which results in interference/s or inhibition/s of the enzymes by the reactants and reaction products thereby slowing down of the reaction rate. The present invention discloses a process whereby the action of the two groups of enzymes is separated thereby resulting in higher overall reaction rates.

In the preferred embodiment of the invention, at least one enzyme from a group of enzymes mentioned above is added sequentially in each of the multi-steps to act on the separated hemicellulose or cellulose, or any mixture of hemicelluloses and celluloses, to convert them to fermentable sugars for the production of ethanol and/or other useful products.

Thus, in the first step, an enzyme mixture, comprising at least one enzyme from the first group of enzymes, with or without one or more accessory or auxiliary enzymes, is reacted with hemicellulose and/or cellulose to obtain soluble oligosaccharides. In the first step, besides the enzymes from the first group, enzymes from the second group can be present in low activities.

In the second step, the enzyme or mixture of enzymes comprises of at least one enzyme from the second group of enzymes, with or without one or more of the enzymes from the first group and/or any accessory or auxiliary enzymes, and acts on reaction mixture obtained from the first step, in the same or different reactor of any type, to obtain the fermentable sugars.

One of the embodiments of invention provides a process of hydrolysis of hemicellulose and/or cellulose and which comprises stepwise action of the enzymes. The two step action minimizes inhibitory effect of the both intermediate and final products on enzymes acting in the both steps, namely inhibitory effect of cellobiose, xylobiose and monosugars on one or more components of cellulase and/or hemicellulase enzymes and, in particular, on endo-glucanases, and cellobiohydrolases and xylobiohydrolases. In the present method, all steps of reaction are carried out in the range of the pH which is favourable to the enzymes, or any mixtures thereof, more suitable results found in the range of pH 4 to 8. The reaction pH in the two steps varies within the indicated limits depending upon the source of enzymes and the same may easily determined by all those skilled in the art.

In another embodiment of the present invention, the temperature of the reaction is in the range of 30° C. to 90° C., and that the operating temperature for a mixture of enzymes depends on the activity and stability profile of the enzymes and may be determined easily by all those skilled in the art. The overall enzymatic hydrolysis is carried out until all hemicellulos and/or cellulose is converted to fermentable sugars.

In accordance with the present invention in one embodiment there is provided a process of production of fermentable sugars from hemicellulose and/or cellulose using multi-step multi-enzyme system, wherein the process comprises treating hemicellulose and/or cellulose with at least one enzyme of first group of enzymes at a temperature ranging from 30° C. to 90° C. to obtain a first hydrolysate, and treating the hydrolysate obtained with at least one enzyme from second group of enzymes to obtain the fermentable sugars; wherein the first group and second group of enzymes are capable of hydrolysing the hemicellulose and/or cellulose.

One embodiment of the present invention provides a process of production of fermentable sugars from hemicellulose and/or cellulose using multi-step multi-enzyme system, wherein the hemicellulose and/or cellulose is substantially free from lignin in particular do not contain more than 10% (w/w) lignin.

In another embodiment of the present invention, there is provided the process of production of fermentable sugars from hemicellulose and/or cellulose using multi-step multi-enzyme system, wherein the process comprises treating hemicellulose and/or cellulose with at least one enzyme of first group of enzymes at a temperature ranging from 30° C. to 90° C. to obtain a first hydrolysate, and treating the hydrolysate obtained with at least one enzyme from second group of enzymes to obtain the fermentable sugars; wherein the first group and second group of enzymes are capable of hydrolysing the hemicellulose and/or cellulose, wherein the first group of enzymes are endo-glucanases, exo-glucanases, endo-xylanases, exo-xylanases, mannanases and galactanases.

In another embodiment of the present invention, there is provided the process of production of fermentable sugars from hemicellulose and/or cellulose using multi-step multi-enzyme system, wherein the process comprises treating hemicellulose and/or cellulose with at least one enzyme of first group of enzymes at a temperature ranging from 30° C. to 90° C. to obtain a first hydrolysate, and treating the hydrolysate obtained with at least one enzyme from second group of enzymes to obtain the fermentable sugars; wherein the first group and second group of enzymes are capable of hydrolysing the hemicellulose and/or cellulose, wherein the second group of enzymes are xylosidases, mannosidases and glucosidases.

In yet another embodiment of the present invention, there is provided the process of production of fermentable sugars from hemicellulose and/or cellulose using multi-step multi-enzyme system, wherein the process comprises treating hemicellulose and/or cellulose with at least one enzyme of first group of enzymes at a temperature ranging from 30° C. to 90° C. to obtain a first hydrolysate, and treating the hydrolysate obtained with at least one enzyme from second group of enzymes to obtain the fermentable sugars; wherein the first group and second group of enzymes are capable of hydrolysing the hemicellulose and/or cellulose, wherein optionally the enzymes are cross-linked with one or more proteins, one or more polymers, or combinations thereof using one or more cross linking agents.

In yet another embodiment of the present invention there is provided protein for cross-linking of enzymes, wherein the protein is selected from a group consisting of first group of enzymes, second group of enzymes, transferrin, globulins, animal serum albumin, soy protein, whey protein and wheat gluten, or any combinations thereof.

In one embodiment, the present invention provides cross-linking agents selected from a group consisting of glutaraldehyde, divinylsulphone, polyethyleneimine, and 1,4-butanedioldiglycidylether.

In still yet another embodiment of the present invention, there is provided the process of production of fermentable sugars from hemicellulose and/or cellulose using multi-step multi-enzyme system, wherein the process comprises treating hemicellulose and/or cellulose with at least one enzyme of first group of enzymes at a temperature ranging from 30° C. to 90° C. to obtain a first hydrolysate, and treating the hydrolysate obtained with at least one enzyme from second group of enzymes to obtain the fermentable sugars; wherein the first group and second group of enzymes are capable of hydrolysing the hemicellulose and/or cellulose, wherein the hemicellulose and/or cellulose converts into the fermentable sugars in batch process in 4 to 8 hours.

In further embodiment of the present invention, there is provided the process of production of fermentable sugars from hemicellulose and/or cellulose using multi-step multi-enzyme system, wherein the process comprises treating hemicellulose and/or cellulose with at least one enzyme of first group of enzymes at a temperature ranging from 30° C. to 90° C. to obtain a first hydrolysate, and treating the hydrolysate obtained with at least one enzyme from second group of enzymes to obtain the fermentable sugars; wherein the first group and second group of enzymes are capable of hydrolysing the hemicellulose and/or cellulose, wherein the hemicellulose and/or cellulose converts into the fermentable sugars in continuous process with hydraulic retention time of 1 to 4 hours.

One embodiment of the present invention provides the fermentable sugars comprising soluble oligosaccharides, cellobiose, glucose, xylobiose, xylose and arabinose.

Another embodiment of the present invention provides a process for obtaining hemicelluloses and/or cellulose from biomass, wherein process comprises mixing the biomass with 5% to 10% (w/v) alkali having pH in the range of 12-14 at a temperature ranging from 50° C. to 200° C. under 1.0 to 20 bar pressure for 5 minutes to 2 hours to obtain a biomass slurry; filtering the biomass slurry to obtain filtrate comprising hemicelluloses and residue comprising cellulose; treating the filtrate with alcohol to obtain a precipitate containing hemicelluloses; washing the residue containing cellulose with water to remove residual alkali to obtain cellulose; and washing the precipitate to obtain hemicelluloses.

Yet another embodiment of the present invention provides a process for obtaining hemicelluloses and/or cellulosed from biomass, wherein the biomass is selected from a group consisting of grasses, rice straw, wheat straw, cotton stalk, castor stalk, sugarcane or sorghum bagasse, corn cobs, corn stover, stalks, switch grass and elephant grass.

Another embodiment of the present invention provides a process for obtaining hemicelluloses and/or cellulosed from biomass using alkali, wherein the ratio of alkali to biomass is 0.5 to 2.0, preferably 1.4.

Another embodiment of the present invention provides a process for obtaining hemicelluloses and/or cellulose from biomass, wherein process comprises mixing the biomass with 5% to 10% (w/v) alkali having pH in the range of 12-14 at a temperature ranging from 50° C. to 200° C. under 1.0 bar pressure for 2 hours to obtain a biomass slurry; filtering the biomass slurry to obtain filtrate comprising hemicelluloses and residue comprising cellulose; treating the filtrate with alcohol to obtain a precipitate containing hemicelluloses; washing the residue containing cellulose with water to remove residual alkali to obtain cellulose; and washing the precipitate to obtain hemicelluloses.

Another embodiment of the present invention provides a process of obtaining hemicelluloses and/or cellulose from biomass, wherein process comprises mixing the biomass with 5% to 10% (w/v) alkali having pH in the range of 12-14 at a temperature ranging from 50° C. to 200° C. under 1.0 to 20 bar pressure for 5 minutes to 2 hours to obtain a biomass slurry; filtering the biomass slurry to obtain filtrate comprising hemicelluloses and residue comprising cellulose; treating the filtrate with alcohol to obtain a precipitate containing hemicelluloses; washing the residue containing cellulose with water to remove residual alkali to obtain cellulose; and washing the precipitate to obtain hemicelluloses, wherein at least 85% hemicellulose is recovered.

Another embodiment of the present invention provides a process of obtaining hemicelluloses and/or cellulose from biomass, wherein process comprises mixing the biomass with 5% to 10% (w/v) alkali having pH in the range of 12-14 at a temperature ranging from 50° C. to 200° C. under 1.0 to 20 bar pressure for 5 minutes to 2 hours to obtain a biomass slurry; filtering the biomass slurry to obtain filtrate comprising hemicelluloses and residue comprising cellulose; treating the filtrate with alcohol to obtain a precipitate containing hemicelluloses; washing the residue containing cellulose with water to remove residual alkali to obtain cellulose; and washing the precipitate to obtain hemicelluloses, wherein at least 90% cellulose is recovered.

Another embodiment of the present invention provides a process of production of fermentable sugars from biomass using multi-step multi-enzyme system, wherein the process comprises
a. mixing biomass with 5% to 10% w/v alkali having pH in the range of 12-14 at a temperature ranging from 50° C. to 200° C. under 1.0 to 20 bar pressure for 5 minutes to 2 hrs to obtain a biomass slurry;
b. filtering said biomass slurry to obtain filtrate comprising hemicellulose; and residue comprising cellulose;
c. treating the filtrate with alcohol to obtain a precipitate containing hemicelluloses;
d. washing the residue from step (b) with water to remove residual alkali to obtain cellulose;
e. washing the precipitate to obtain hemicelluloses;
f. treating the hemicellulose from step (e) and/or the cellulose from step (d) with at least one enzyme of first group of enzymes at a temperature ranging from 30° C. to 90° C. to obtain a hydrolysate; and
g. treating the hydrolysate of step (f) with at least one enzyme from second group of enzymes to obtain the fermentable sugars
wherein the first group and second group of enzymes are capable of hydrolysing the hemicellulose and/or cellulose Further embodiment of the present invention provides a process of production of fermentable sugars from biomass using multi-step multi-enzyme system, wherein the process comprises
a. mixing biomass with 5% to 10% w/v alkali having pH in the range of 12-14 at a temperature ranging from 50° C. to 200° C. under 1.0 to 20 bar pressure for 5 minutes to 2 hrs to obtain a biomass slurry;
b. filtering said biomass slurry to obtain filtrate comprising hemicellulose; and residue comprising cellulose;
c. treating the filtrate with alcohol to obtain a precipitate containing hemicelluloses;
d. washing the residue from step (b) with water to remove residual alkali to obtain cellulose;
e. washing the precipitate to obtain hemicelluloses;
f. treating the hemicellulose from step (e) and/or the cellulose from step (d) with at least one enzyme of first group of enzymes at a temperature ranging from 30° C. to 90° C. to obtain a hydrolysate; and
g. treating the hydrolysate of step (f) with at least one enzyme from second group of enzymes to obtain the fermentable sugars
wherein the first group and second group of enzymes are capable of hydrolysing the hemicellulose and/or cellulose; wherein the first group and second group of enzymes are cross-linked with a protein or a polymer using a cross-linking agent.

In another embodiment of the present invention the enzymes are recycled and reused to provide a cost effective process in terms of cost of the enzyme used per unit of hemicellulose and/or cellulose hydrolyzed to fermentable sugars. For example, the enzymes can be used in packed, stirred, or fluidized bed reactors in immobilized form, or in membrane reactors, or combinations thereof.

An immobilized enzyme is an enzyme which is attached to an inert, insoluble, porous or non-porous, material. This can provide increased stability and resistance of the enzymes to changes in conditions such as shear, pressure, pH or temperature. Immobilization also allows enzymes to be held in place, or in the confines of the reactor throughout the reaction, following which they are easily separated from the products and may be used again.

Immobilized enzymes are cost effective as well as simple to use in more than one cycle. The immobilized enzyme is easily removed from the reaction making it easy to recycle the biocatalyst. Immobilized enzymes typically have greater thermal and operational stability than the soluble form of the enzyme. Immobilized enzymes can be prepared by different methods. A widely used method is adsorption of the enzymes on a suitable solid porous matrix. Enzyme is attached to the solid surface of the matrix by a variety of methods ranging from simple adsorption to covalent reaction. The enzyme can also be trapped in insoluble beads or microspheres, such as calcium alginate beads. However, these insoluble substances hinder the arrival of the substrate, and the exit of products, especially when the substrate is polymeric and bulky molecule.

The enzyme can also be covalently bonded to a matrix or any enzyme/protein through a chemical reaction. This method is by far the most effective method among those listed here. As the chemical reaction ensures that the binding site does not cover the enzyme's active site, the activity of the enzyme is only affected by immobility. The enzyme and the matrix are cross-linked through a cross-linking agent such glutaraldehyde or carbodiimide.

According to one of the preferred embodiments of the current invention, the enzyme is immobilized on a suitable solid support. The carriers or matrix used for immobilization may comprise of any natural or synthetic and organic or inorganic material e.g. hydrophilic synthetic polymer such as polyacrylamides, polymethacrylamides, polyacrylates, polymethacrylates, polyimides, polyvinyl hydrophilic polymers, polystyrene, polysulfone or the like and natural or synthetic polysaccharides such as starch, dextran, chitin agar or agarose; inorganic material such as silicious materials such as silicon dioxide including amorphous silica and quartz, controlled pore glass, titanium dioxide and ceramics or suitable combination thereof.

In another embodiment of the present invention, the enzyme/s can be cross-linked with itself or any other protein, or any other monomer or polymer, by means of a cross-linking agent, to form soluble or insoluble aggregates called cross-linked enzyme aggregates (CLEA), and that can be used as immobilized enzyme, or in membrane reactors wherein, the membranes are able to retain the enzymes or enzyme aggregates as well as polymeric substrates, while permitting smaller reaction products to permeate or pass through.

In another embodiment of the invention, when using enzymes to act upon solid substrate, like cellulose in solid form the process cost is rendered cost effective through the recycling of the enzyme/s, the enzyme/s being used in membrane reactors as macromolecules in their native form, or cross-linked to itself, or to a suitable protein/enzyme, or any other monomer or polymer, using a suitable cross-linking agent to obtain active cross-linked soluble enzyme preparations with 100% membrane rejection coefficients. The proteins used for cross-linking are transferrin, globulins, animal serum albumins, soy protein, whey protein, and wheat gluten.

According to one of the preferred embodiment of the present invention, the saccharification process, for cellulose and hemicellulose, separately or combined, is carried out in bioreactors and the bioreactors used for the First step and/or Second step can be packed bed or fluidized bed bioreactors, or stirred tank bioreactors that are coupled with membrane filtration systems using micro-filtration, ultra-filtration membranes, and/or nano-filtration membranes.

According to another preferred embodiment of the current invention, hemicellulose is treated with at least one of the enzymes of the first group of enzyme, wherein the enzyme/s breaks down the polymeric structure of hemicellulose to soluble oligosaccharides. Further, in the second step these oligosaccharides are treated with at least one of the enzymes from the second group, wherein the enzyme/s convert soluble oligosaccharides to fermentable sugars.

According to another embodiment of the present invention, the first step of saccharification of hemicelluloses is carried out in a stirred tank bioreactor which is coupled with a membrane filtration system, such as microfiltration, ultrafiltration and/or nanofiltration, preferably ultrafiltration membrane alone, which retains and recycles soluble enzyme/s of the first step to the tank bioreactor, and soluble oligosaccharides pass through it. The second step is carried out in the second stirred tank bioreactor, which is coupled with yet another membrane filtration system, such as ultrafiltration or nanofiltration, preferably nano-filtration membrane which retains and recycle soluble enzyme/s of the second step as well as the larger soluble oligosaccharides while fermentable sugars will pass through as permeate.

According to another embodiment of the present invention, the First step of saccharification of hemicelluloses is carried out in a packed bed reactor wherein the enzyme/s used in the first step are immobilized on a suitable matrix. Soluble oligosaccharides are formed in the reactor that goes to the second step. The Second step is carried out in the second packed bed reactor column containing immobilized enzymes from the second group of enzymes to obtain fermentable sugars. Alternatively, the second reactor is a stirred tank bioreactor, which is coupled with a membrane filtration system, such as ultrafiltration or nanofiltration, preferably ultrafiltration, which retains and recycles soluble enzyme/s of the second group as well as large oligosaccharides while fermentable sugars are obtained as permeate.

According to another embodiment of the present invention, the First step of saccharification of hemicelluloses is carried out in a bioreactor, which is coupled with a membrane filtration, such as ultrafiltration or nanofiltration, preferably ultrafiltration, which will retain soluble enzyme/s used in the first step and also the larger soluble and insoluble oligosaccharides. Soluble oligosaccharides pass through the membrane, and in the second step contacted with immobilized enzyme/s of the second group in a packed bed reactor and converted to fermentable sugars.

According to another embodiment of the present invention, the First step of saccharification of hemicelluloses is carried out in a packed bed reactor wherein the enzyme/s used in the first step are immobilized on a suitable matrix. Soluble oligosaccharides are formed and passed through a second column/bioreactor, wherein the enzyme/s of the Second group are immobilized on a suitable matrix. The stream emerging from the second column reactor contains fermentable sugars.

According to another preferred embodiment of the current invention, cellulose, is treated in the First step with at least one of the enzymes of the first group of enzyme and/or some enzymes from the second group, wherein the enzyme/s breaks down basic polymeric structure of cellulose to oligosaccharides. Further in the Second step these oligosaccharides are treated with at least one of the enzymes from the second group and/or some enzymes from the other group, and wherein these enzyme/s convert oligosaccharides to fermentable sugars.

One of the embodiments of invention is that oligosaccharides formed during saccharification of cellulose, in particular cellobiose, have an inhibitory effect on the enzymes and, in particular, on endo-gluconases and cellobiohydrolases. Further, glucosidases convert cellobiose to glucose which can also inhibit glucanases. Such inhibitory effect can be minimized by the two step treatment of the enzymes.

In another embodiment of the present invention, the enzyme/s of the first step can be cross-linked with the high molecular weight protein, or any other monomer, or polymer, by means of a cross-linking agent. Cellulose is an insoluble solid and hence it is unlikely that the immobilization of the enzymes would help the enzyme action. Thus to make the process of saccharification of cellulose cost effective through the recycling of the enzyme of the first step, first group of enzymes are cross-linked to a protein or polymer by a suitable cross-linking agent.

In another embodiment of the present invention, the first group of enzyme/s used for saccharification of cellulose is cross-linked with the same enzyme/s or proteins such as transferrin, globulins, animal serum albumin, soy protein, whey protein, or wheat gluten.

In another embodiment of the present invention, the cross-linking agent used are from a group consisting of glutaraldehyde, divinylsulphone, polyethyleneimine, and 1,4-butanedioldiglycidylether.

In one of the preferred embodiment of the present invention, the First step of saccharification of cellulose is carried out in a stirred tank reactor which is coupled with the membrane separation assembly to retain and recycle the soluble/ cross-linked enzyme/s used in the first step. The membrane separation assembly may include microfiltration, ultrafiltration or nanofiltration membranes, to retain enzymes and sugar polymers, while soluble oligosaccharides pass through the membranes and are sent through the second reactor containing enzyme from the second group. This second stirred tank reactor is also coupled with a membrane separation assembly which may include ultrafiltration membranes or nanofiltration membranes, that retain enzymes and large oligosaccharides while smaller fermentable sugars pass through the membranes.

In another embodiment of the present invention, the First step of saccharification of cellulose is carried out in a bioreactor which is coupled with the membrane separation assembly to retain the soluble native or cross-linked enzyme/s from the first group. The membrane separation assembly may include ultrafiltration membranes or nanofiltration membranes, to retain and recycle enzymes and larger oligosaccharides while smaller oligosaccharides pass through these membranes and are sent through the second column reactor. The Second step is carried out in the second column or bioreactor, wherein the enzyme/s of the second step is immobilized on a suitable matrix. These enzymes convert soluble oligosaccharides to fermentable sugars.

According to another preferred embodiment of the current invention, a mixture of hemicellulose and cellulose, is treated in the First step with at least one of the enzymes of the first group of enzyme and/or some enzymes from the second group, wherein the enzyme/s breaks down basic polymeric structure of hemicellulose and cellulose to oligosaccharides. Further in the Second step these oligosaccharides are treated with at least one of the enzymes from the second group and/or some enzymes from the other group, and wherein these enzyme/s convert oligosaccharides to fermentable sugars.

It is often required to conduct simultaneous saccharification of hemicellulose and cellulose in order to obtain a combined hydrolysate in a single two step enzyme reactor assembly for subsequent single step and combined fermentation of sugars obtained to desired products like ethanol. In such cases, the hemicellulose and cellulose obtained from biomass are processed as a mixture for hydrolysis and saccharification steps. The basic logic behind the two step enzyme reaction of the present invention however, is found to be as applicable to the mixture of hemicellulose and cellulose as to each single component.

One of the embodiments of invention is that oligosaccharides formed during saccharification of hemicellulose and cellulose, in particular cellobiose and xylobiose, have an inhibitory effect on the enzymes and, in particular, on endoglucanases and biohydrolases. Further, glycosidases convert bioses to monosugars and these can also inhibit glucanases. Such inhibitory effect can be minimized by the two step treatment of the enzymes.

In another embodiment of the present invention, the enzyme/s of the first step can be cross-linked with the high molecular weight protein, or any other monomer, or polymer, by means of a cross-linking agent. Cellulose is an insoluble solid and hence it is unlikely that the immobilization of the enzymes would help the enzyme action. Thus to make the process of saccharification of a mixture of hemicellulose and cellulose cost effective through the recycling of the enzyme of the first step, the first group of enzymes are cross-linked to a protein or polymer by a suitable cross-linking agent.

In another embodiment of the present invention, the first group of enzyme/s used for saccharification of the mixture of hemicellulose and cellulose is cross-linked with the same enzyme/s or proteins such as transferrin, globulins, animal serum albumin, soy protein, whey protein, or wheat gluten.

In another embodiment of the present invention, the cross-linking agent used are from a group consisting of glutaraldehyde, divinylsulphone, polyethyleneimine, and 1,4-butanedioldiglycidylether.

In one of the preferred embodiment of the present invention, the First step of saccharification of mixture of hemicellulose and cellulose is carried out in a stirred tank reactor which is coupled with the membrane separation assembly to retain and recycle the soluble or cross-linked enzyme/s used in the first step. The membrane separation assembly may include microfiltration, ultrafiltration or nanofiltration membranes, to retain enzymes and sugar polymers, while soluble oligosaccharides pass through the membranes and are sent through the second stirred tank reactor containing enzyme from the second group. This second reactor is also coupled with a membrane separation assembly which includes ultrafiltration membranes or nanofiltration membranes that retain enzymes and large oligosaccharides while smaller fermentable sugars pass through the membranes.

In another embodiment of the present invention, the First step of saccharification of a mixture of hemicellulose and cellulose is carried out in a stirred tank reactor which is coupled with the membrane separation assembly to retain the soluble native or cross-linked enzyme/s from the first group. The membrane separation assembly includes ultrafiltration membranes or nanofiltration membranes, to retain and recycle enzymes and larger oligosaccharides while smaller oligosaccharides pass through these membranes and are sent through the second column reactor. The Second step is carried out in the second column reactor, wherein the enzyme/s of the second step is immobilized on a suitable matrix. These enzymes convert soluble oligosaccharides to fermentable small sugars. The reactor assemblies used and described above for carrying out the process according to the present invention are varied to meet any particular requirements. Thus, the hydrodynamics of the reaction is maintained to ensure optimal conversion of product solution by laminar flow and by keeping minimal shear in the stirred, membrane and packed reactors.

The following examples are given by the way of illustration of the invention contained in the present invention and therefore should not be construed to limit the scope of the present invention.

EXAMPLES

It should be understood that the following examples described herein are for illustrative purposes only and that various modifications or changes in light of the specification will be suggestive to person skilled in the art and are to be included within the spirit and purview of this application and the scope of the appended claims.

Example 1

Preparation of Hemicelluloses from Cotton Stalks 3 gm of dried and size reduced cotton stalk is treated with 100 ml of 5% alkali at 121° C. for 30 minutes in an autoclave or pressure reactor. The treated sample is filtered to remove the solid residue. The filtrate containing hemicelluloses is treated with 500 ml absolute ethanol. The precipitate obtained was filtered and washed with excess ethanol to obtain hemicellulose as a buff colored powder.

Example 2

Preparation of Cellulose and Hemicelluloses+Cellulose Mixture from Rice Straw 1 gm of dried and size reduced cotton stalk is treated is 20 ml of 5% alkali at 121° C. for 15 minutes in an autoclave. The treated sample is filtered and washed with water to recover the solid residue as cellulose fraction. The filtrate containing hemicellulose is treated with 50 ml absolute ethanol, and the precipitate obtained is filtered and washed with excess ethanol to obtain hemicellulose as a buff colored precipitate. The cellulose residue and hemicellulose so obtained are mixed to give mixture of hemicellulose and cellulose for further processing.

Example 3

Hydrolysis of Hemicellulose (a) Batch Reaction without Enzyme Recycle

Hemicellulose (40 g) in 1000 mL of 50 mM citrate buffer pH 5 was treated with 4000 IU of a pre-dominantly endo-xylanase enzyme at 50° C. for 2 hours. One unit of enzyme is defined as the micromoles of product given by one milliliter of enzyme per minute. Gel permeation Chromatography showed that xylobiose was the major product. In the second step 2000 IU of xylosidase enzyme was used as the second group of enzymes and added to the reaction medium. Complete conversion of hemicellulose to xylose was obtained over within next 2.0 hours. Table 1 gives the details of the reaction process with HM1 being the first enzyme and HMII being the second enzyme.

(b) Continuous Hemicellulose Hydrolysis with Enzyme Recycle

A 3% w/v suspension of hemicellulose in 50 mM citrate buffer pH 5.0 was added at about 10 mL/min using a metering pump so as to maintain the liquid level at a constant height in a 500 mL jacket heated stirred reactor wherein a total of 1000 IU of endo-xylanase was also added in one lot initially. The stirred reactor was maintained at 50° C. and coupled with a membrane filtration system. The entire reactor assembly consisted of a stirred tank reactor (500 mL) equipped with a peristaltic pump that circulated the reaction mass through a tubular ultrafiltration membrane system (5 KDa and 0.01 square meter). The retentate from the membrane system was sent back to the stirred tank while the permeate was collected in beaker from which another peristaltic pump passed the reaction mass through a packed bed of immobilized beta-xylosidase (10 mm dia×500 mm H). The flow rate of the permeate and column was maintained at 10 mL/min. The flow from the second reactor was analysed for glucose content. 95% conversion of hemicellulose to monosugars was found to occur on continuous steady state basis. An overall average hydraulic retention time of 40-50 minutes was maintained.

Example 4

Hydrolysis of Mixture of Hemicellulose and Cellulose (a) Batch Reaction without Enzyme Recycle The mixture of hemicellulose and cellulose (40 g) was suspended in acidified water (pH 5) and was treated with a 4000 IU of mixture of endo- and exo-glucanases at 50° C. for 2.0 hour. One unit of enzyme is defined as micromoles of glucose equivalent reducing sugars produced per milliliter of enzyme per minute. Gel permeation chromatography of reaction mixture after 2 hours showed that soluble oligosaccharides are the major products formed. The second step reaction was carried out using a mixture of beta-glucosidase and beta-xylosidase (each 1000 IU) was added to the reaction mixture from the first step. Complete conversion of polysaccharides to glucose and xylose was obtained within next 2.0 hours. The results of the reaction progress are given in Table 2.

(b) Continuous Reaction with Enzyme Recycle

A 4% w/v suspension of a mixture of hemicellulose and cellulose (in a ratio of 3:7) in acidified water (pH 5) was added at about 15 mL/min using a metering pump so as to maintain the liquid level at a constant height in a 500 mL jacket heated stirred reactor to which was added in one lot 1000 IU of mixture of endo- and exo-glucanases. The stirred tank temperature was maintained at 50° C. The membrane reactor assembly was same as the one mentioned in Example 3(b). The stirred reactor was coupled with a membrane filtration system. The retentate from the membrane system was sent back to the stirred tank while the permeate was collected in beaker from which another peristaltic pump passed the reaction mass through a packed bed of mixture of immobilized beta-glucosidase and immobilized beta-xylosidase (10 mm diameter×500 mm H). The flow rate of the permeate and column was maintained at 15 mL/min. The flow from the second reactor was analysed for glucose content. An average of 90% combined conversion to monosugars was found to occur on continuous steady state basis. An overall average hydraulic retention time of 40-50 minutes was maintained.

Example 5

Hydrolysis of Cellulose (a) Batch Hydrolysis of Cellulose

Cellulose (10 g) was suspended in 50 mM citrate buffer pH 4.8 and was treated with 1000 IU of mixture of endo- and exo-cellulases in a stirred reactor at 50° C. One unit of enzyme is defined as the micromoles of product given by one milliliter of enzyme per minute. The GPC showed that oligosaccharides are major products after 2.0 hrs. Then in the second step, beta-glucosidase (500 IU) was added to reaction medium. Complete conversion of cellobiose to glucose is over within next 2.0 hours.

(b) Continuous Hydrolysis of cellulose with enzyme recycle

A 3% w/v suspension of cellulose in 50 mM citrate buffer pH 5.0 was added at about 10 mL/min using a metering pump so as to maintain the liquid level at a constant height in a 500 mL jacket heated stirred reactor wherein a total of 1000 IU of mixture of endo- and exo-cellulases was added to the stirred tank and the reaction conducted at 50° C. The reactor assembly consisted of a stirred tank reactor equipped with a peristaltic pump that circulated the reaction mass through a tubular ultrafiltration membrane system (5 KDa and 0.01 square meters). The retentate from the membrane system was sent back to the stirred tank while the permeate was collected in beaker from which another peristaltic pump passed the reaction mass through a packed bed of immobilized beta-glucosidase (10 mm diameter×500 mm H). The flow rate of the permeate and column was maintained at 15 mL/min. The flow from the second reactor was analysed for glucose content. 90% conversion of cellulose to glucose was found to occur on continuous steady state basis. An overall average hydraulic retention time of 40-50 minutes was maintained.

Example 6

Preparation of Crosslinked Cellulase

The mixture of exo-glucanase and/or endo-glucanase having a total activity of 10 IU was crosslinked with soy protein isolate (2 mg/ml) prepared in the laboratory using glutaraldehyde as cross-linking agent under alkaline conditions. The cross-linking reaction period was controlled to obtain soluble preparation enzyme aggregates (as evidenced on native PAGE). The preparation was diafiltered and concentrated on a 30 KDa ultrafiltration membrane in order to remove non-cross-linked proteins and excess cross-linking agent. The liquid preparation containing 50 mg/mL protein was used as the enzyme preparation.

Example 7

Continuous Hydrolysis of Cellulose Using Cross-linked Cellulase

A 3 % w/v suspension of pure cellulose in 50 mM citrate buffer pH 5.0 was added at about 10mL/min using a metering pump so as to maintain the liquid level at a constant height in a 500 mL jacket heated stirred reactor wherein a total of 1000IU equivalent of cross-linked exoglucanase and endo-glucanase activity was added to the stirred tank which was maintained at 45° C. The reaction mixture was continuously recirculated through a 30 KDa ultrafiltration membrane. The permeate was passed through a packed bed column containing immobilized enzyme as used in Example 5 (b). The reaction mixture from the packed column reactor was analysed for glucose content. An average conversion of about 90% conversion of cellulose to glucose was found to occur on continuous steady state. An overall average hydraulic retention time of 40 -50 minutes was maintained.

TABLE 1

Comparison of the rate and extent of enzymatic hydrolysis of hemicellulose using two hemicellulase enzyme preparations HMI and HMII, each predominantly containing enzymes from the first group and the second group, respectively.

| | | Saccharification percentage in hours | | | | |
|---|---|---|---|---|---|---|
| | Enzymes | 1 | 2 | 3 | 4 | 24 |
| Experiment 1 | HM I + HM II at start | ND | 70 | ND | 80 | 100 |
| Experiment 2 | HM I (1 hr) followed by HM II | 37 | 78 | 84 | 86 | 100 |
| Experiment 3 | HM I (2 hr) followed by HM II | ND | 56 | 84 | 100 | — |

Experiment 1 is the traditional case where the two enzyme preparations were used together, and Experiments 2 and 3 are where the two enzyme preparations have been used in two steps as described in the present invention.

TABLE 2

Comparison of the rate and extent of enzymatic hydrolysis of cellulose + hemicellulose in the ratio 64:20 using two cellulase enzyme preparations cellulase and cellulase + glucosidase, each predominantly containing enzymes from the first group and the second group, respectively.

| | Percentage Saccharification | |
|---|---|---|
| Reaction time (hrs) | Experiment 1: Cellulase | Experiment 2: Cellulase + Glucosidase |
| 1 | 60.5 | 62.0 |
| 2 | 63.7 | 81.0 |
| 4 | 68.8 | 96.4 |
| 6 | 71.6 | 98.1 |

Experiment 1 is the traditional case where the two enzyme preparations were used together, and Experiments 2 is where the two enzyme preparations have been used in two steps as described in the present invention.

We claim:

1. A process of production of fermentable sugars from cellulose using a multi-step multi-enzyme system, said process comprising
   (a) treating cellulose with endo-glucanases and exo-glucanases at a temperature ranging from 30° C. to 90° C. to obtain a hydrolysate;
   (b) separating the hydrolysate from the endo-glucanases and exo-glucanases enzymes to obtain a solution comprising oligosaccharides, cellobiose, and glucose; and
   (c) treating the solution with glucosidases to obtain the fermentable sugars.

2. The process as claimed in claim 1, wherein the cellulose do not contain more than 10% (w/w) lignin.

3. The process as claimed in claim 1, wherein endo-glucanases, exo-glucanases or glucosidases are cross-linked with one or more proteins, one or more polymers, or combinations thereof using one or more cross linking agents.

4. The process as claimed in claim 3, wherein the cross linking agent is selected from a group consisting of glutaraldehyde, divinylsulphone, polyethyleneimine, and 1,4-butanedioldiglycidylether.

5. The process as claimed in claim 1, wherein the cellulose converts into the fermentable sugars in a batch process in 4 to 8 hours.

6. The process as claimed in claim 1, wherein the cellulose converts into the fermentable sugars in continuous process with hydraulic retention time of 1 to 4 hours.

7. The process as claimed in claim 1, wherein the fermentable sugars comprise soluble oligosaccharides, cellobiose, and glucose.

8. The process as claimed in claim 1, wherein the cellulose is obtained by a process comprising
   a. mixing biomass with 5% to 10% w/v alkali having pH in the range of 12-14 at a temperature ranging from 50° C. to 200° C. under 1.0 to 20 bar pressure for 5 minutes to 2 hours to obtain a biomass slurry;
   b. filtering said biomass slurry to obtain a residue comprising cellulose; and
   c. washing the residue from step (b) with water to remove residual alkali to obtain cellulose.

9. The process as claimed in claim 8, wherein the biomass is selected from the group consisting of grasses, rice straw, wheat straw, cotton stalk, castor stalk, sugarcane or sorghum bagasse, corn cobs and corn stover, stalks, switch grass, and elephant grass.

10. The process as claimed in claim 8, wherein the ratio of alkali to biomass is 0.5: 2.0.

11. The process as claimed in claim 8, wherein said pressure is 1.0 bar.

12. The process as claimed in claim 8, wherein said time is 2 hrs.

13. The process as claimed in claim 8, wherein at least 90% cellulose is recovered.

14. The process as claimed in claim 8, wherein the ratio of alkali to biomass is 1:4.

15. A process of production of fermentable sugars from biomass using a multi-step multi-enzyme system, said process comprising
   (a) mixing biomass with 5% to 10% w/v alkali having pH in the range of 12-14 at a temperature ranging from 50° C. to 200° C. under 1.0 to 20 bar pressure for 5 minutes to 2 hours to obtain a biomass slurry;
   (b) filtering said biomass slurry to obtain a residue comprising cellulose;
   (c) washing the residue from step (b) with water to remove residual alkali to obtain cellulose;
   (d) treating the cellulose from step (c) with endo-glucanases and exo-glucanases at a temperature ranging from 30° C. to 90° C. to obtain a hydrolysate;
   (e) separating the hydrolysate from the endo-glucanases and exo-glucanases enzymes to obtain a solution comprising oligosaccharides, cellobiose, and glucose; and
   (f) treating the solution with glucosidases to obtain the fermentable sugars.

* * * * *

UNITED STATES PATENT AND TRADEMARK OFFICE
CERTIFICATE OF CORRECTION

PATENT NO. : 8,338,139 B2
APPLICATION NO. : 13/305063
DATED : December 25, 2012
INVENTOR(S) : Arvind Mallinath Lali et al.

Page 1 of 1

It is certified that error appears in the above-identified patent and that said Letters Patent is hereby corrected as shown below:

On the Title Page: Item (30)

In the left column, insert a new item as follows:

-- Foreign Application Priority Data

| May 29, 2009 | (IN) | 1314/MUM/2009 |
| May 26, 2009 | (IN) | 1299/MUM/2009 --. |

Signed and Sealed this
Twenty-fifth Day of June, 2013

Teresa Stanek Rea
*Acting Director of the United States Patent and Trademark Office*